United States Patent [19]

Iwashita et al.

[11] 4,412,989

[45] Nov. 1, 1983

[54] OXYGEN CARRIER

[75] Inventors: Yuji Iwashita, Kawasaki; Katsumi Ajisaka, Yokohama; Keiji Iwasaki, Kawasaki, all of Japan

[73] Assignee: Ajinomoto Company Incorporated, Tokyo, Japan

[21] Appl. No.: 384,606

[22] Filed: Jun. 3, 1982

[30] Foreign Application Priority Data

Jun. 10, 1981 [JP] Japan ................................. 56-89315

[51] Int. Cl.$^3$ ..................... A61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS 4,301,144 11/1981 Iwashita et al. .................... 424/177

OTHER PUBLICATIONS

The Journal of Biological Chemistry 255, No. 19, (1980), 8975–8978.
Biochemical and Biophysical Research Communication 97, (1980), 1076–1081.
Chem. Abstr., vol. 96, (1982), 62768x.

*Primary Examiner*—Delbert R. Phillips
*Attorney, Agent, or Firm*—Oblon, Fisher, Spivak, McClelland & Maier

[57] ABSTRACT

An oxygen carrying material containing hemoglobin or a hemoglobin derivative covalently coupled through an amide bond to a polymer selected from the group consisting of polyethylene glycol, polypropylene glycol, and copolymers of ethylene oxide and propylene oxide.

12 Claims, No Drawings

OXYGEN CARRIER

The present invention relates to a novel oxygen carrier, more particularly to hemoglobin coupled to a polymer, such as a polyether selected from the group consisting of polyethylene glycol, polypropylene glycol, copolymer of ethylene oxide and propylene oxide, for use as an oxygen carrier in a blood substitute. The improvement is that said hemoglobin is attached to said polymer (hereinafter referred to as the polymer of the present invention) through an amide bond.

It is known that the hemoglobin covalently coupled to a polymer selected from the group consisting of polyethylene glycol, polypropylene glycol, and a copolymer of ethylene oxide and propylene oxide is useful as an oxygen carrier for a blood substitute, from the Japanese first publication No. 12308/1981 and U.S. Pat. No. 4,301,144.

The substance of the present invention for oxygen carrier as a blood substitute can be prepared, for example, by combining hemoglobin with the polymer of the present invention, in which at least one carboxyl group is incorporated, through an amide bond.

The polymer of the present invention is, for example, polyethylene glycol, polypropylene glycol or a copolymer of ethylene oxide and propylene oxide, and includes an ether of one of the above mentioned polyalkylene glycols and an alcohol having a carbon number of 1 to 16, such as monomethyl ether, monocetyl ether and monooleyl ether; an ester of one of the above polyalkylene glycols and a carboxylic acid having a carbon number of 2 to 18, such as monobutyl ester and monostearyl ester, and a dehydrated product of one of the above polyalkylene glycols and an amine having a carbon number of 1 to 18, such as propyl amine and stearyl amine.

The molecular weight of the polyether is 300 to 20,000, preferably 750 to 10,000 in the view from efficiency and viscosity.

As a process for introducing carboxylic groups in the polyether, for example, there can be employed the known method as described in U.S. Pat. Nos. 4,179,337 and 3,941,710 specifications, or the method for attaching at least one carboxylic acid of a polycarboxylic acid such as alkane dicarboxylic acid to a terminal hydroxyl group of the polyether to give an ester of the polycarboxylic acid.

In a reaction of the polymer, into which the carboxyl group has been introduced, with hemoglobin, for example, there can be employed a method of conventional peptide synthesis, such as one using N-hydroxy succinimide, N-hydroxy phthalimide, p-nitrophenol or pentachlorophenol, to give the product with hemoglobin through an amide bond or the method of treating the carboxylated polyether with a halogenating agent such as thionyl chloride to give acid halide of the polymer having at least one carboxyl group, and then combining the product with hemoglobin.

Examples of polycarboxylic acids mentioned above are malonic acid, succinic acid, glutaric acid, adipic acid, malic acid, and citric acid. The oxygen carrying ability of the homoglobin-polymer complexes in the present invention is not deteriorated by introducing carboxylic groups into the complexes.

The hemoglobin used in the present invention includes hemoglobin obtained from animals such as cattle, swine, sheep, horses, dogs, monkeys or chickens, as well as human beings, and further includes hemoglobin derivatives of pyridoxal 5'-phosphate, pyridoxal 5'-sulfate, 2-Nor-2-Formyl pyridoxal 5'-Phosphate, 2,3-diphospho glyceric acid, inositol penta-or hexaphosphate or a sugar having a carboxylic group or phosphate group.

In the hemoglobin combined with the polymer of the present invention through amide bonding, the number of the polymer attached (Substitution degree) and molecular weight of a given hemoglobin complex, were determined by the method of Ajisaka et al. (K. Ajisaka and Y. Iwashita, Biochem. Biophys. Res. Commun. 97, 1076–1081, 1981). Thereby, from 1 to 20 molecules of, for example, polyether carboxylic acids are attached to a given hemoglobin (subunit).

The hemoglobin-polymer complex bound through an amide bond can be prepared according to the following methods.

(1) polyether carboxylic acid and 1 to 10 times moles, preferably 2 times mole, of N-hydroxy succinimide are dissolved in N,N-dimethyl formamide in the presence of 1 to 10 times mole, preferably 2 times mole, dicyclohexyl carbodiimide for 3 to 20 hours, preferably 8 to 14 hours, at a room temperature or under heating. Precipitated dicyclohexyl urea is removed by filtration. By adding ethyl ester to the filtrate, the activated ester of polyether carboxylic acid is obtained. The activated ester is allowed to react with about 1 to 1/100 time mole, preferably 1/5 to 1/30 time mole, of hemoglobin or the hemoglobin derivative at pH 6.5–9.5, preferably pH 7–8.5, in an aqueous solution or a buffer solution.

In the reaction N-hydroxy phthalimide, p-nitrophenol or pentachloro-phenol can be employed in place of N-hydroxy succinimide and almost the same result can be obtained.

(2) Polyether carboxylic acid and 1 to 10 times mole, preferably 5 times mole, of imidizol are dissolved in N,N-dimethyl formamide. To this mixture 1 to 10 times mole, preferably 5 times mole, of dicyclohexyl carbodiimide are added and reacted for 5 to 20 hours, preferably 10 hours, under refluxing. After the mixture is cooled, the generated dicyclohexyl urea is removed by filtration. By adding ethyl ether to the filtrate, the activated polyether carboxylic acid ester is obtained.

This activated polyether carboxylic acid ester is allowed to react with about 1 to 1/100 time mole, preferably 1/5 to 1/30 time mole, of hemoglobin or the hemoglobin derivative at pH 7–9, preferably pH 7.5–8.5, in an aqueous solution or in a buffer solution.

In the last reaction, succinimide or phthalimide in place of imidazole can be employed and thereby almost the same result can be obtained.

In order to activate the carboxylic acid, the polyether carboxylic acid may be allowed to react with 1 to 10 times mole, preferably 2 times mole, of carbonyl diimidazole in N,N-dimethyl formamide.

(3) Polyether carboxylic acid can react with excess of thionyl chloride for from 1 to 5 hours, preferably 1.5 to 2 hours, at temperature of 60° to 90° C., preferably 75° C. to 80° C. Thionyl chloride is removed by distillation under reduced pressure, and thus obtained polyether carboxylic acid halide is allowed to react with 1/10 to 1/100 time mole, preferably 1/30 to 1/50 time mole, of hemoglobin or hemoglobin derivative at pH 8.5–9.5, in an aqueous solution or a buffer solution.

In the above reaction, acid halogenating agent such as phosphorus oxychloride or phosphorus pentachloride in place of thionyl chloride may be employed.

The safety of the modified hemoglobin of the present invention is proved by the exchange transfusion experiment.

Rats which exchange-transfused more than 90% of their blood with the 6% solution of the modified hemoglobin of the the present invention survived, whereas rats which were exchange transfused with 6% bovine serum albumin solution died before the exchange ratio reached to 82%. This result proved the absence of the acute toxicity of the present modified hemoglobin, and $LD_{50}$ was estimated over 4.5 g/kg. The present invention is further illustrated by the following examples.

EXAMPLE 1

Five gram (0.001 mole) of monomethoxy polyethylene glycol succinate of which the mean molecular weight is 5,000 and 0.23 g (0.002 mole) of dicyclohexyl carbodiimide were dissolved in 300 ml of N,N-dimethyl formamide and the mixture solution was stirred overnight at room temprature.

The precipitated dicyclohexyl urea was separated by filtration. To the filtrate was added 600 ml of ethyl ether, and thereby the monomethoxy polyethylene glycol mono(succinimidyl succinate) in a crystalline form was separated by filtration and washed well with ethyl ether. 4.6 g of white crystals were obtained.

0.5 g (0.1 milli mole) of the activated polyether ester was added at 0° C. to the solution obtained by dissolving 0.5 g (0.0077 milli mole) of a hemoglobin derivative of pyridoxal-5'-phosphate in 100 ml of phosphate buffer solution of pH 8.5. The mixture was stirred for 4 hours at 0° C. The product was purified by repeated ultrafiltration with a membrane of which molecular weight cut-off is 30,000 dalton, and thereby unreacted activated ester and decomposed materials were removed, and a modified hemoglobin solution was obtained.

This product showed single peak by high speed liquid chromatography using TSK G3000 SW column (Toyo Soda Co., Inc. Japan).

The product was freeze-dried and 0.58 g of modified hemoglobin was obtained.

Substitution degree: 6.0.
Molecular weight: 95,000.

The substitution degree and molecular weight were estimated assuming that the modified hemoglobin formed a tetramer ($\alpha_2\beta_2$).

EXAMPLE 2

Two gram (1 milli mole) of polyethylene glycol adipate of which the mean molecular weight is 2,000, 0.27 g (1 milli mole) of pentachloro phenol and 0.25 g (1.2 milli mole) of dicyclohexyl carbaodiimide were added in 30 ml of N,N-dimethyl formamide overnight at room temperature. The precipitated dicylohexyl urea was filtrated off.

Crystals precipitated by adding ethyl ether to the filtrate were separated by filtration and the product was re-crystalized from toluene to give 1.5 g of crystals.

0.22 g (0.1 milli mole) of the activated ester as mentioned above was added slowly to 20 ml of 0.05% aqueous carbonylhemoglobin solution.

In this case, pH of the solution was kept at 8.5 with 0.2 N solution hydroxide aqueous solution.

The reaction mixture was ultrafiltrated repeatedly with a membrane of which a molecular weight cut-off is 30,000 dalton, and thereof 2 ml of 0.4% modified hemoglobin solution was obtained.

This material showed a single peak by high speed liquid chromatography,

Substitution degree: 3.5.
Molecular weight: 72,000.

EXAMPLE 3

8.5 g (0.015 mole) of polyethylene glycol monocarboxymethyl ether of which the mean molecular weight is 850, 2.07 g (0.015 mole) of para-nitrophenol and 2.3 g (0.015 mole) of dicyclohexylcarabodiimide were dissolved in 300 ml of N,N-dimethyl formamide and reacted overnight at room temperature.

Dicyclohexyl urea was separated by filtration. 600 ml of ethyl ether was poured to the filtrate to generate 6.2 g of crystals.

The activated ester as mentioned above reacted with 10 ml of the hemoglobin derivative of glucose 6-phosphate (1% solution) in the same procedure as in Example 1, and thereby, 10.5 ml of 0.8% modified hemoglobin solution was obtained.

Substitution degree: 6.2.
Molecular weight: 70,000.

EXAMPLE 4

Four gram (0.002 mole) of monomethoxy polyethylene glycol succinate (molecular weight is 2,000) and 0.7 g (0.004 mole) of N,N-carabodiimidazole were dissolved and were allowed to react in 100 ml of N,N-dimethyl formamide overnight at room temperature. Two hundred milliliter of ethyl ether was poured into the reaction mixture and the precipitate was separated by filtration and washed well with ethyl ether to give monomethyoxy polyethylene glycol imidazole succinate (yield: 2.2 g). Six milliliter (0.0055 milli mole) of a 6% solution of a hemoglobin derivative of pyridoxal 5'-phosphate was added in 60 ml of 0.1 M Tris buffer solution of pH 8.0, and to the solution 1 g (0.5 milli mole) of the imide was added.

After 4 hours reaction in an ice bath, the product was ultrafiltrated repeatedly with a membrane of which molecular weight cut-off is 30,000 dalton, and thereby 3.6 ml of 8.3% modified hemoglobin aqueous solution was obtained.

Substitution degree: 10.4.
Molecular weight: 86,000.

EXAMPLE 5

Five gram (0.001 mole) of monomethoxy polyethylene glycol succinate (molecular weight 5,000), 0.5 g (0.005 g mole) of succinimide and 1 g (0.005 mole) of dicyclohexyl carbodiimide were dissolved in 50 ml of N,N-dimethyl formamide, and the reaction mixture was refluxed for 12 hours.

The dicyclohexyl urea was filtered off. To the filtrate, 150 ml of ethyl ether was added and the precipitate was separated by filtration. The precipitate was washed well with ethyl ether and dried to give 3.2 g of crystal.

3.8 ml of 4.8% modified hemoglobin solution was obtained by the reaction of the imide as mentioned above with 7 ml of the hemoglobin derivative of pyridoxal 5'-phosphate (concentration 3.2%) in the same procedure as in Example 4.

Substitution degree: 11.2.
Molecular weight: 120,000.

EXAMPLE 6

5.2 gram (0.001 mole) polyethylene glycol monocarboxymethyl ether of which the mean molecular weight was 5,200, was dissolved in 20 ml of thionyl chloride and heated for 1.5 hours at temperature of 75°–80° C.

Unreacted thionyl chloride was removed by distillation under reduced pressure. The obtained acid chloride salt in a crystalline form was dried well. Twenty milliliter of 1% solution of carbonylhemoglobin derivative of pyridoxal 5′-phosphate was dissolved in 200 ml of 0.7 M borate buffer solution of pH 10.0. To the solution 5 g of the acid chloride mentioned above was added slowly at 0° C.

After 3 hours stirring at 0° C., the reaction mixture was ultrafiltrated repeatedly with a membrane with a cut-off molecular weight of 50,000 dalton, and thereby 4.6 ml of 4.1% modified hemoglobin solution was obtained.

Substitution degree: 9.3.
Molecular weight: 114,000.

EXAMPLE 7

One hundred grams (0.025 mole) of polyethylene glycol (molecular weight 4,000) and 6.3 g (0.063 mole) of succinic acid anhydride were dissolved in 100 ml of N,N-dimethylformamide. The mixture was stirred for 3 hours at 100° C. and then the reaction mixture was cooled.

To the mixture 400 ml of ethyl ether was added, and the obtained precipitate was separated by filtration, washed well with ethyl ether, and dried, and 97.5 g of polyethylene glycol disuccinate was obtained as crystals.

97.5 g (0.024 mole) of crystalline mentioned above, 6.3 g (0.054 mole) of N-hydroxysuccinimide, and 11.4 g (0.054 mole) of dicyclohexyl carbodiimide were dissolved in 100 ml of N,N-dimethylformamide under heating, and then stirred overnight at 30° C. The precipitated dicyclohexyl urea was separated by filtration.

Polyethylene glycol bis(succinimidyl succinate) in a crystalline form, produced by adding 300 ml of ethyl ether to the filtrate, was separated by filtration, washed well with ethyl ether and dried to give 95 g of white crystals.

10 milliliter (0.025 milli mole) of 16.4% hemoglobin solution was poured into 35 ml of borate buffer solution of pH 8.5. To the mixture 4.3 g (1.0 milli mole) of crystalline polyethylene glycol bis (succinimidyl succinate) was added. The mixture was stirred overnight at 4° C.

The product was purified by repeated ultrafillration with the use of a membrane having a molecular weight cut-off of 100,000 dalton, and thereby 51 ml of 3.2% modified hemoglobin aqueous solution was obtained.

Substitution degree: 11.2.
Molecular weight: 122,000.

EXAMPLE 8

14.3 ml (0.1 milli mole) of 15% solution of hemoglobin derivative of pyridoxal-5′-phosphate was added to 270 ml of phosphate buffer solution of pH 7.0.

In this solution 4.43 g (1.1 milli mole) of crystalline polyethylene glycol bis(succinimidyl succinate) was added slowly at 4° C.

The mixture was stirred for 4 hours at 4° C., and then the product was purified by repeated ultrafiltration with a membrane having a molecular weight cut-off of 100,000 dalton, and thereby 11 ml of 11.6% modified hemoglobin solution was obtained.

Substitution degree: 6.6.
Molecular weight: 93,000.

EXPERIMENT 1

As to the hemoglobin-polyether complexes prepared in the above Examples, oxygen dissociation curves were measured by the method of Imai et al. (K. Imai, H. Morimoto M. Kotani, H. Watari, H. Waka and M. Kuroda, Biochim. Biophys. Acta. 200, 189–196, 1970), and therefrom the oxygen partial pressure, at which half of the hemoglobin is saturated with oxygen ($P_{50}$ value), was estimated. The results were collected in Table 1.

By use of same hemoglobin-polyether complexes, the residence time in the circulation was measured as follows. Two rats (weighing about 350 g) were used for one measurement. The rats were infused with 5 ml of 4–6% hemoglobin-polyether complex solution per kg of body weight through the femoral vein, and 0.2 ml of blood was withdrawn at 5, 10, 15, 30, 60, 90 and 120 minutes after the injection. Each blood sample was centrifuged, and the concentration of hemoglobin in the plasma was determined by the cyanomethemoglobin method.

The half resistant time for each sample was estimated from a graph of the change in concentration against the time after the injection. The results were given in Table 1.

TABLE 1

| Sample Example No. | $P_{50}$ value*2 (mm Hg) | Half Residence Time (minute) |
|---|---|---|
| 1 | 8.8 | 150 |
| 2*1 | 3.6 | 120 |
| 3 | 4.3 | 150 |
| 4 | 4.4 | 180 |
| 5 | 9.8 | 250 |
| 6*1 | 3.1 | 220 |
| 7 | | |
| 8 | 3.0 | 170 |
| 9 | 7.7 | 160 |
| The hemoglobin polyether complex of Example 2 in U.S. Pat. No. 4,301,144 | 13.5 | 120 |
| Hemoglobin, free (control) | 8.7 | 35 |

*1Carbon monoxide was removed under oxygen stream, and thereafter $P_{50}$ value and Half residence time were determined.
*2 25° C., pH 7.4, 0.1N NaCl From these results the half residence time of the hemoglobin-polyether complexes of the present invention in the rat circulation was from 4 to 7 times as long as that of hemoglobin itself. Furthermore, these substances have a remarkable ability to deliver oxygen to the tissues of the organs.

EXPERIMENT 2

As to the hemoglobin-polyether complex prepared in Example 5 of the present invention and Example 4 in the U.S. Pat. No. 4,301,144, the Bohr Effect was measured according the method of Bucci and Fronticelli (E. Bucci and C. Fronticelli, Method in Enzymology, vol. 76, 523–533 (1981)). The results were shown in Table 2.

TABLE 2

| Sample | Bohr. coefficient* |
|---|---|
| Example 5 in this invention | 0.33 |
| Example 4 in U.S. Pat. No. 4,301,144 | 0.12 |

TABLE 2-continued

| Sample | Bohr. coefficient* |
|---|---|
| Hemoglobin, free (Control) | 0.48 |

*25° C., 0.1M phosphate buffer

From the results of Table 2, the Bohr Effect of the modified hemoglobin of the present invention is about 3 times larger than that of the modified hemoglobin in the U.S. Pat. No. 4,301,144. Consequently this result means that the former has superior ability of transporting the carbon dioxide from the tissues to the lung than the latter.

EXPERIMENT 3

As to the 6% solution of the hemoglobin-polyether complexes prepared in the Examples 1, 7, 9 of this invention and Example 6 in the U.S. Pat. No. 4,301,144, the colloidal osmotic pressure was measured. The results are shown in Table 3.

TABLE 3

| Sample | Colloidal Osmotic Pressure* (mm Hg) |
|---|---|
| Example 1 of this invention | 39.4 |
| Example 7 of this invention | 42.5 |
| Example 9 of this invention | 38.8 |
| Example 6 of U.S. Pat. No. 4,301,144 | 156.6 |
| Blood (control) | 31.0 |

*The colloidal osmotic pressure was measured with a 4100 colloid Osmometer (Wescor Inc.) at 25° C.

From the above results, it was shown that the colloidal osmotic pressure of the samples in this invention is more suitable for transfusion than the sample in U.S. Pat. No. 4,301,144.

The substances of the present invention are superior from the viewpoints of ability to carry carbon dioxide from the tissues to the lung and of safety (because of its low colloidal osmotic pressure).

Therefore, the substances of the present invention are very useful for oxygen carriers as blood substitute.

What is claimed is:

1. An oxygen carrying material containing hemoglobin or a hemoglobin derivative covalently coupled through an amide bond to a polymer selected from the group consisting of polyethylene glycol, polypropylene glycol, and copolymers of ethylene oxide and propylene oxide.

2. The material of claim 1 wherein a hydroxyl group of said polymer is substituted with an alcohol having a carbon number of 1 to 16, a carboxylic acid having a carbon number of 2 to 18, or an amide having a carbon number of 1 to 18, and hemoglobin or a hemoglobin derivative is coupled to said polymer through an amide bond.

3. The material of claim 1 wherein hemoglobin is coupled to said polymer through an amide bond by the help of a carboxylic acid.

4. The material of claim 3 wherein said carboxylic acid is selected from the group consisting of monohalogenated carboxylic acids and dicarboxylic acids.

5. The material of claim 1 wherein said hemoglobin is modified with pyridoxal, a phosphate or sulfate containing derivative of pyridoxal, a sugar phosphate, 2,3-phosphoglyceric acid, or a sugar derivative containing a carboxylic acid group.

6. The material of claim 5 wherein said derivative of pyridoxal is pyridoxal-5'-phosphate, pyridoxal-5'-sulphate, or 2-Nor-2-formylpyridoxal-5'-phosphate.

7. The material of claim 5 wherein said sugar phosphate is glucose-6-phosphate.

8. The material of claim 1 wherein said polymer has a molecular weight of 300 to 20,000.

9. The material of claim 8 wherein said molecular weight is 750 to 10,000.

10. In a method of carrying oxygen to animal tissues by use of an oxygen carrier, the improvement which comprises using the oxygen carrying material of claim 1 as an oxygen carrier.

11. A method of preparing a hemoglobin-polymer complex for an oxygen carrier as a blood substitute by chemical reaction, in which the polymer is selected from the group consisting of polyethylene glycol, polypropylene glycol, and copolymers of ethylene oxide and propylene oxide, comprising:
   (1) introducing at least one carboxylic acid group to said polymer to give a carboxylic acid-containing polymer, and
   (2) coupling the carboxylic acid-containing polymer through an amide bond with an amino group of hemoglobin or a hemoglobin derivative.

12. The method of claim 11 wherein a carboxylic acid selected from the group consisting of monohalogenated carboxylic acids and dicarboxylic acids is reacted with said polymer to introduce said carboxylic acid group.

* * * * *